US006190365B1

(12) United States Patent
Abbott et al.

(10) Patent No.: US 6,190,365 B1
(45) Date of Patent: Feb. 20, 2001

(54) VAGINAL DOUCHE APPLICATOR AND METHOD OF VAGINAL DEODORIZATION USING THE SAME

(76) Inventors: Chun Lim Abbott; Dominic C. Abbott, both of 708 Squaw Run Rd., E., Pittsburgh, PA (US) 15238

( * ) Notice: Under 35 U.S.C. 154(b), the term of this patent shall be extended for 0 days.

(21) Appl. No.: 09/336,724

(22) Filed: Jun. 21, 1999

(51) Int. Cl.[7] ...................................................... A61N 31/00
(52) U.S. Cl. ............................................ 604/279; 604/515
(58) Field of Search ............................ 604/39, 264, 275, 604/279, 257, 515, 359

(56) References Cited

U.S. PATENT DOCUMENTS

| | | | | |
|---|---|---|---|---|
| 4,176 | | 9/1845 | Harrington . | |
| 7,668 | | 7/1833 | Harrington . | |
| 7,982 | | 1/1834 | Harrington . | |
| 8,736 | | 3/1835 | Harrington . | |
| 77,539 | | 5/1868 | Schevenell et al. . | |
| 362,778 | | 5/1887 | Payne . | |
| 471,514 | | 3/1892 | Reutter . | |
| 494,520 | | 3/1893 | Boyd . | |
| 505,393 | | 9/1893 | Dawdy et al. . | |
| 520,206 | | 5/1894 | Hinkley . | |
| 520,895 | | 6/1894 | Petit . | |
| 527,788 | | 10/1894 | Hebard . | |
| 563,387 | | 7/1896 | Keller . | |
| 625,143 | | 5/1899 | Busky . | |
| 635,004 | | 10/1899 | Souder . | |
| 662,716 | | 11/1900 | Gaedeke . | |
| 932,775 | | 8/1909 | Gaston . | |
| 1,042,624 | | 10/1912 | Wagoner . | |
| 1,098,220 | * | 5/1914 | Borsody . | |
| 1,149,971 | | 8/1915 | Wagoner . | |
| 1,195,933 | | 8/1916 | Wagoner . | |
| 3,479,130 | | 11/1969 | Rapaport . | |
| 4,701,164 | * | 10/1987 | Cassou et al. | 604/218 |
| 4,923,677 | * | 5/1990 | Simon et al. . | |
| 4,950,231 | * | 8/1990 | Liu | 604/39 |
| 5,695,481 | * | 12/1997 | Heinzelman et al. | 604/279 |
| 5,946,741 | * | 9/1990 | Moon . | |

OTHER PUBLICATIONS

The Odor Steeler™ from iSi North America, product catalog, pp. 1–2, Mar. 19, 1999.

* cited by examiner

*Primary Examiner*—Richard K. Seidec
*Assistant Examiner*—LoAn H. Thanh

(57) ABSTRACT

A vaginal douche applicator includes an applicator body for positioning in the vaginal canal and comprising an elongate body portion and a tip disposed at a distal end of the body portion. The body portion has an open proximal end for being coupled with a source of a douching fluid that includes water, and the tip defines a closed distal end for the applicator body. The applicator body has a fluid passage therein communicating with the open proximal end for receiving the douching fluid from the source. A plurality of discharge holes are formed in the applicator body in communication with the fluid passage by which the douching fluid is discharged from the fluid passage into the vaginal canal. The body portion has an external surface of stainless steel for contacting vaginal tissue whereby vaginal odors are neutralized due to contact of the tissue with the stainless steel in the presence of the water of the douching fluid supplied to the vaginal canal through the applicator. The tip forms a protuberance for sealingly engaging the vaginal wall to deter douching fluid supplied to the vaginal canal through the applicator from passing distally beyond the tip such that the douching fluid is deterred from entering the cervical canal. A method of vaginal deodorization includes the steps of introducing a vaginal douche applicator into the vaginal canal, supplying water to the vaginal canal through the applicator and contacting vaginal tissue with a stainless steel surface of the applicator as the water is supplied to the vaginal canal such that vaginal odors are neutralized.

17 Claims, 4 Drawing Sheets

VAGINAL DOUCHE APPLICATOR AND METHOD OF VAGINAL DEODORIZATION USING THE SAME

BACKGROUND OF THE INVENTION

1. Field of the Invention

The present invention relates generally to vaginal douches and, more particularly, to a vaginal douche applicator for neutralizing vaginal odors due to contact of vaginal tissue with the applicator in the presence of water introduced through the applicator, to a vaginal douche applicator having a protuberance for deterring the entry of douching fluid into the cervical canal and to a method of vaginal deodorization using a vaginal douche applicator.

2. Brief Description of the Related Art

In the area of female personal hygiene and gynecological health, vaginal douches have been proposed for reducing and/or eliminating vaginal odors. Conventional vaginal douches typically involve the application of a stream of douching fluid to the vaginal canal of the user. Since water alone as a douching fluid is not effective in significantly alleviating vaginal odors or the sources, such as bacteria, of vaginal odors, conventional vaginal douches typically include various douching agents or substances such as cleansing and/or disinfecting agents and/or perfumes. Accordingly, various commercially prepared douching agents or substances have been proposed for being mixed with water to obtain a douching fluid. One problem associated with conventional vaginal douches is that the douching agents or substances may cause irritation in some users and tend to alter the normal acid/alkaline or chemical balance of the vaginal canal. When the vaginal canal of a woman becomes irritated and/or has the normal acid/alkaline or chemical balance thereof disturbed or altered, the woman may be at increased risk for vaginitis, such as yeast, trich and other infections. Vinegar has been used as a douching agent or substance which, when mixed with water in the proper proportions, presents a douching fluid that closely mimics the normal pH of the vaginal canal. However, vinegar and water douches tend not to be effective against vaginal odors for any meaningful length of time. Furthermore, vaginal douches are typically applied with vaginal douche applicators for introduction in the vaginal canal of the user and through which the douching fluid is forcefully introduced into the vaginal canal. Conventional vaginal douche applicators have the disadvantage of allowing the douching fluid introduced therethrough into the vaginal canal to enter the cervical canal and even the uterine cavity of the user. Since the douching fluid entering the uterine cavity and/or the cervical canal may contain bacteria and/or other infectious organisms picked up in the vaginal canal, conventional vaginal douche applicators are associated with an increased risk of cervical, uterine and/or pelvic infections, such as cervicitis and pelvic inflammatory disease. In addition, conventional vaginal douches may not be effective in alleviating some vaginal odors or may serve merely to temporarily mask the vaginal odors. Even when conventional vaginal douches are effective in alleviating vaginal odors, the vaginal odors may return shortly after douching. Accordingly, although conventional vaginal douches and vaginal douche applicators are generally convenient and easy to use, the benefits derived from conventional vaginal douches may be outweighed by the problems and disadvantages associated therewith in that conventional vaginal douches and vaginal douche applicators may actually do more harm than good.

The use of stainless steel under running water to remove odors from the hands has also been proposed, as represented by the NOnion® of 5K Enterprises, Allison Park, Pa. the Odor Steeler™ of iSi North America. Such devices include a body made of stainless steel which, when rubbed on the hands under running water, causes odors such as onion, garlic, poultry, fish, seafood and nicotine to be removed from the hands without soap or harsh scrubbing. The devices, which have configurations similar to bars of soap, do not have any passages therein through which fluid may be supplied.

In view of the above, it can be seen that the need exists for alternative vaginal douches and vaginal douche applicators which are convenient and easy to use but which overcome the various problems and disadvantages of conventional vaginal douches and vaginal douche applicators. It can be seen that the need further exists for vaginal douches that are effective in neutralizing vaginal odors without employing added douching agents or substances and while allowing only water to be used as the douching fluid. Another need made apparent from the above is for a vaginal douche applicator that has a configuration to deter the passage of douching fluid into the uterine cavity and/or the cervical canal of a user.

Until the present invention, the foregoing needs have not been met or satisfied. In particular, the use of stainless steel in the presence of water to neutralize vaginal odors has not been previously recognized or contemplated. Accordingly, it has not previously been recognized to introduce water into the vaginal canal through a douche applicator having a stainless steel surface and to neutralize vaginal odors by contact of the stainless steel surface with the anatomical tissue of the vaginal canal in the presence of the water. It has also not been possible until the present invention to effectively alleviate vaginal odors via douching, with only water as the douching fluid without any added douching agents or substances. Prior to the present invention, a vaginal douche applicator having a configuration to deter the passage of douching fluid into the uterus and/or the cervical canal has also not been proposed.

SUMMARY OF THE INVENTION

Accordingly, it is a primary object of the present invention to overcome the aforementioned disadvantages of vaginal douches and vaginal douche applicators and methods of deodorizing or neutralizing odors of the vaginal canal by douching.

Still another objective of the present invention is to deodorize anatomical tissue by contact of the tissue with a stainless steel surface of an applicator body in the presence of water supplied to the tissue through the applicator body.

Another object of the present invention is to neutralize vaginal odors by douching, wherein the douching fluid is waterwithout any extraneous douching substances oragents added thereto.

A further object of the present invention is to neutralize vaginal odors by contacting vaginal tissue with a surface of stainless steel while water is applied to the vaginal tissue.

An additional object of the present invention is to contact vaginal tissue with a stainless steel surface of a douche applicator while applying water to the vaginal tissue through the douche applicator.

It is also an object of the present invention to deter the passage of douching fluid into the cervical canal during vaginal douching.

The present invention has as another object to obstruct the vaginal canal with a protuberance of a vaginal douche applicator such that douching fluid forcefully supplied to the vaginal canal through the douche applicator is deterred from entering the cervical canal.

Additionally, the present invention has as an object to obstruct the external cervical os with a protuberance of a vaginal douche applicator such that douching fluid forcefully supplied to the vaginal canal through the douche applicator is inhibited from entering the cervical canal.

Yet a further object of the present invention is to introduce douching fluid into the vaginal canal through a vaginal douche applicator and to facilitate discharge of the douching fluid from the vaginal canal while the douche applicator is disposed in the vaginal canal.

Some of the advantages of the present invention are that household water alone is rendered effective in neutralizing vaginal odors without the addition of or combination with extraneous douching agents or substances within the vaginal canal or externally thereof, vaginal odors are neutralized without altering the normal acid/alkaline or chemical balance of the vaginal canal, complications of douching, such as irritation and infections, are reduced or eliminated, vaginal odors are neutralized more effectively than with conventional vaginal douches and the neutralization of vaginal odors as a result of vaginal douching in accordance with the present invention lasts or endures for a greater length of time.

These and other objects, advantages and benefits are realized with the present invention as generally characterized in a vaginal douche applicator including an applicator body for positioning in the vaginal canal and comprising an elongate body portion and a tip disposed at a distal end of the body portion. The body portion has an open proximal end for being coupled with a source of douching fluid that includes water, and the tip defines a closed distal end for the applicator body. A fluid passage is disposed within the applicator body in communication with the open proximal end for receiving the douching fluid from the source. A plurality of discharge holes are formed in the applicator body in communication with the fluid passage by which the douching fluid is discharged from the fluid passage into the vaginal canal. The applicator body has an external surface of stainless steel for contacting tissue of the vaginal wall whereby vaginal odors are neutralized due to contact of the tissue with the stainless steel in the presence of the water of the douching fluid discharged into the vaginal canal from the vaginal douche applicator.

A preferred vaginal douche applicator according to the present invention includes a protuberant tip forming a protuberance or enlargement at the distal end of the body portion. The protuberant tip forms a seal with the vaginal wall deterring douching fluid discharged from the discharge holes into the vaginal canal from passing distally beyond the tip whereby the douching fluid is deterred from entering the cervical canal.

A method of vaginal deodorization according to the present invention includes the steps of introducing a vaginal douche applicator in the vaginal canal, supplying water to the vaginal canal through the applicator and contacting the tissue of the vaginal canal with a stainless steel surface of the applicator as the water is supplied to the vaginal canal such that vaginal odors are neutralized due to contact of the tissue with the stainless steel in the presence of the water.

Other objects and advantages of the present invention will become apparent from the following description of the preferred embodiments taken in conjunction with the accompanying drawings, wherein like parts in each of the several figures are identified by the same reference characters.

DESCRIPTION OF THE PREFERRED EMBODIMENTS

Figure 1:
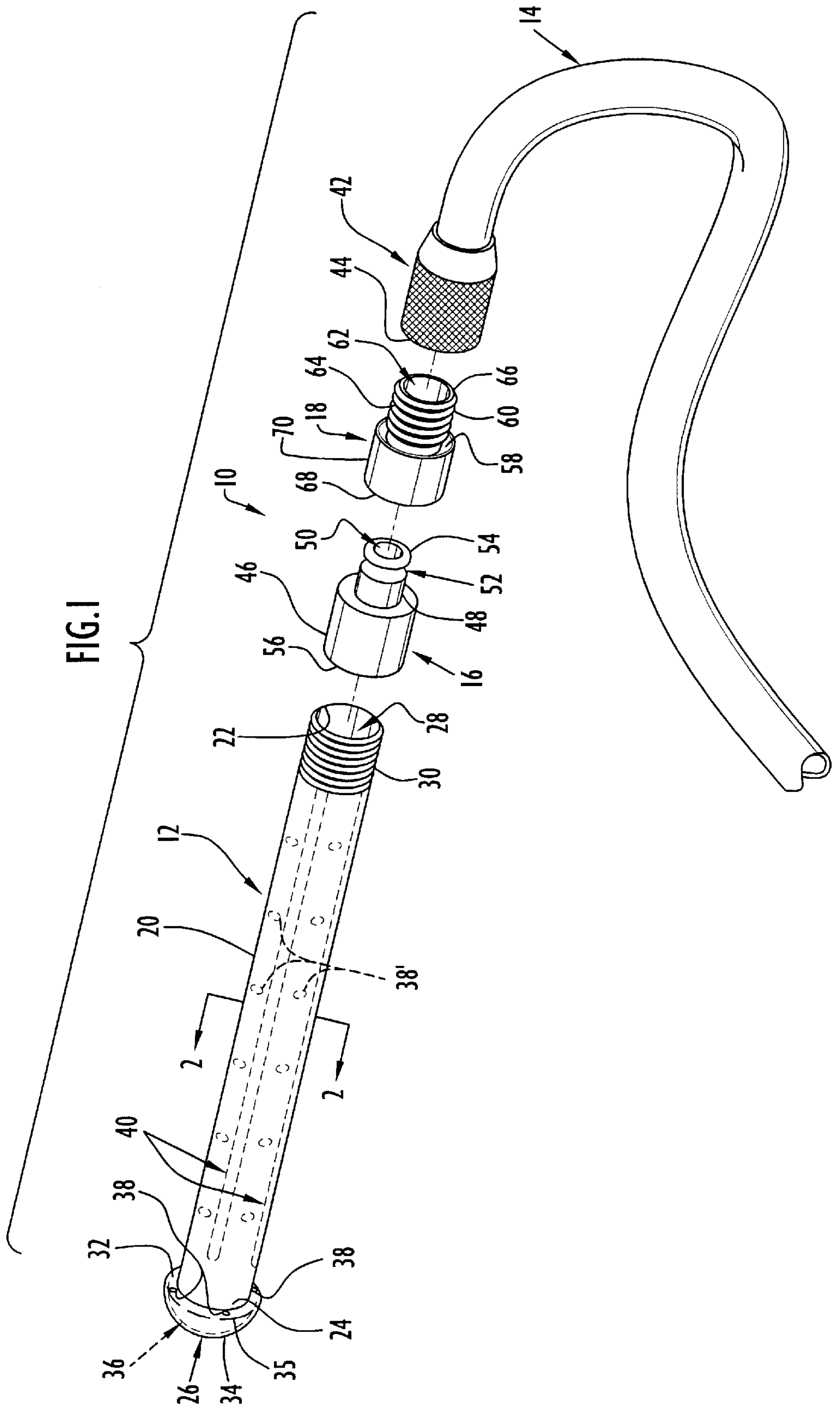
FIG. 1 is an exploded perspective view of a vaginal douche applicator assembly incorporating a vaginal douche applicator according to the present invention.
Figure 2:
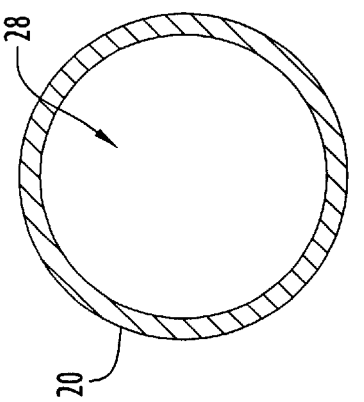
FIG. 2 is a cross-sectional view of a body portion of the vaginal douche applicator taken along line 2—2 of FIG. 1 and illustrating a cross-sectional configuration for the body portion.

An anatomical tissue deodorizer according to the present invention is illustrated in FIG. 1 as a vaginal douche applicator assembly 10. Vaginal douche applicator assembly 10 includes a vaginal douche applicator 12 according to the present invention, a flexible fluid supply tube or hose 14, an adapter 16 for being received on a proximal end of the douche applicator 12 and a coupling 18 for being connected to an end of fluid supply tube 14 and being engageable with the adapter 16 to couple the douche applicator 12 to the fluid supply tube 14. The douche applicator 12 includes an applicator body comprising an elongate body portion 20 having a proximal end 22 and a distal end 24, and a protuberant tip 26 provided on or formed as part of the distal end 24. The body portion 20 has a cylindrical configuration and is hollow or tubular with a longitudinal lumen or internal fluid passage 28 extending entirely therethrough as shown in FIGS. 1 and 2. Accordingly, the proximal end 22 and the distal end 24 of body portion 20 are open, and the open proximal end 22 defines the proximal end of the applicator body. The proximal end 22 is provided with an external thread 30 for securement of the proximal end 22 in an internally threaded recess of adapter 16 as explained further below. The body portion 20 is longitudinally or axially straight. However, it should be appreciated that the body portion can be longitudinally or axially curved in accordance with anatomical characteristics of the user. The proximal end 22 can be formed integrally, unitarily with the body portion 20, or the proximal end can be formed as a separate piece or part secured to the body portion 20. As an example, the proximal end 22 can be formed as an externally threaded sleeve or collar disposed on the cylindrical body portion 20 such as with a compression fit. In the preferred embodiment, body portion 20 is without external grooves as shown in FIGS. 1 and 2; however, an alternative embodiment for the body portion includes one or more longitudinally extending external grooves as explained further below.

The tip 26 protrudes beyond the body portion 20, in a direction transverse to a longitudinal axis of the body portion 20, to define a protuberance or enlargement adjacent the distal end 24 of body portion 20. The tip 26 includes an annular end flange 32 disposed around and connected to the distal end 24 of body portion 20 and a convex or partial spherical, solid forward wall 34 extending distally from flange 32. The end flange 32 extends laterally or transversely beyond an external circumferential or diametric dimension of body portion 20 and has an external circumferential dimension concentric with an external circumferential dimension of the body portion 20. The end flange 32 is joined to or merges with the forward wall 34 along its external circumferential dimension, which is greater than the external circumferential dimension of body portion 20 . An external circumferential edge or rim 35 along which the end flange 32 is joined to or merges with the forward wall 34 is preferably rounded or blunt to avoid damage, trauma, irritation or other harm or injury to vaginal tissue. The tip 26 closes off the open distal end 24 of body portion 20, and the tip 26 defines a closed distal end for the applicator body. The tip 26 is hollow and defines an internal cavity 36, shown in dotted lines in FIG. 1, in communication with the open distal end 24 of body portion 20. Accordingly, the fluid passage 28 of body portion 20 is in communication with the cavity 36 of tip 26.

A plurality of fluid discharge holes or apertures 38 are formed in the applicator body. The holes 38 are disposed adjacent the distal end 24 of the body portion 20 and, in particular, are formed in end flange 32 at spaced locations about the external circumferential dimension of body portion 20. The holes 38 extend through the end flange 32 and establish communication with the cavity 36 from externally of the applicator 12. In the case of vaginal douche applicator 12, a plurality of holes including four holes 38 (three of which are visible in FIG. 1) are provided in end flange 32 at 90° spaced locations about the longitudinal axis of body portion 20. The tip 26 can be formed integrally, unitarily with body portion 20 as a single piece or part, or the tip 26 and the body portion 20 can be formed as separate pieces or parts connected together to form the applicator body. The external circumferential dimension of tip 26 is of a size to sealingly engage or to be sealingly engaged by the vaginal wall when the applicator body is disposed in the vaginal canal during use as explained below.

As shown in dotted lines in FIG. 1, one or more additional fluid discharge holes or apertures 38' can be provided in body portion 20 in communication with the fluid passage 28 and can be disposed or arranged on body portion 20 in various ways. In FIG. 1, a plurality of additional holes 38' are shown in body portion 20, the holes 38' being arranged as a first set of longitudinally spaced and aligned holes 38' and a second set of longitudinally spaced and aligned holes 38' disposed from the first set of holes 38' at a 90° spaced location about the longitudinal axis of body portion 20. Of course, additional sets of holes 38' can be provided in body portion 20 at 90° spaced locations from the first and second sets of holes 38'.

Figure 3:
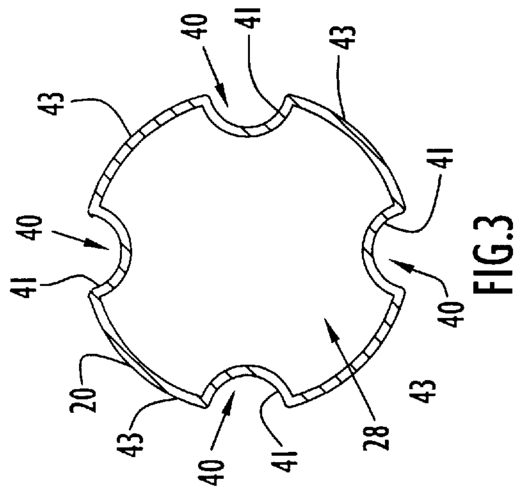
FIG. 3 is a cross-sectional view, similar to that of FIG. 2, illustrating a cross-sectional configuration for the body portion of the vaginal douche applicator having external grooves.

As shown in FIG. 3 and in dotted lines in FIG. 1, one or more external, longitudinally extending grooves 40 can be formed in body portion 20. As an example, four grooves 40 can be externally formed on body portion 20 at 90° spaced locations about the longitudinal axis of body portion 20. As shown by way of example in FIG. 1, each groove 40 is disposed at a radial location between the radial locations at which adjacent holes 38 are disposed relative to the longitudinal axis such that the grooves 40 are staggered with respect to the holes 38. In addition, FIG. 1 is illustrative of a groove 40 being disposed between adjacent sets of holes 38'. The grooves 40 can extend longitudinally or lengthwise along the body portion 20 a desired longitudinal distance or length. Where a plurality of grooves 40 are provided, the grooves 40 can be of the same or different lengths. As shown by way of example in FIG. 1, the grooves 40 extend distally from the thread 30 to terminate at groove ends spaced proximally from the distal end 24 of body portion 20. The grooves 40 can be formed in body portion 20 in many various ways, the grooves 40 being formed by indenting the body wall of body portion 20.

In FIG. 3, the body portion 20 is formed by a body wall of uniform or constant thickness indented to form the grooves 40. Accordingly, the body portion 20 illustrated in FIG. 3 is made up of four concave body wall segments 41 defining grooves 40 and four convex body wall segments 43 coincident with the circumference of body portion 20 with each concave body wall segment 41 being disposed between a pair of adjacent convex body wall segments 43. Accordingly, where the body portion 20 is formed as illustrated in FIG. 3, the fluid passage 28 does not have a circular cross-section. Preferably, the convex body wall segments 43 are connected to the concave body wall segments 41 at rounded or blunt external or outside corners, which define opposed lateral edges for grooves 40, to avoid damage, trauma, irritation or other harm or injury to anatomical tissue of the vaginal canal during use as described further below.

Figure 4:
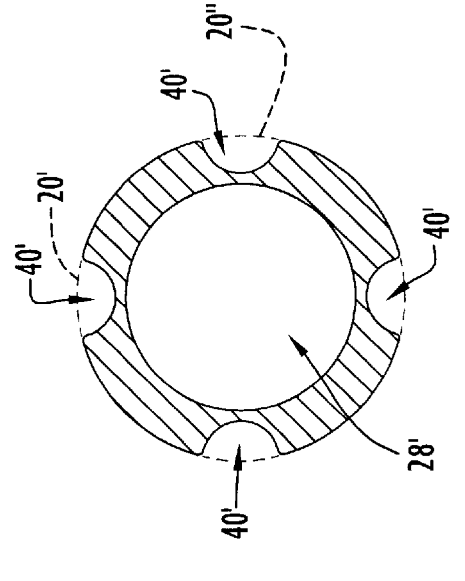
FIG. 4 is a cross-sectional view, similar to that of FIG. 2 illustrating an alternative cross-sectional configuration for a body portion having external grooves.

FIG. 4 illustrates an alternative cross-sectional configuration for a body portion of applicator 12 having grooves. In FIG. 4, the body portion 20' is defined by a body wall of non-uniform thickness since the grooves 40' are formed as notches or cut-outs extending part way through the thickness of the body wall. Accordingly, the fluid passage 28' for body 20' has a circular cross-sectional configuration in FIG. 4. As pointed out above, it is preferred that the lateral edges of the grooves 40' be rounded or blunt to avoid tissue damage, trauma, irritation or other harm or injury during use. Although the body wall is illustrated in FIG. 4 as being thicker than the body wall illustrated in FIG. 3, it should be appreciated that the body wall can have any desired thickness. Minimizing the thickness of the body wall may be preferred, however, in order to minimize the weight of the applicator body and to reduce material requirements and, therefore, manufacturing costs. It should be further appreciated that the applicator body can be provided without grooves indicated by way of example in dotted lines at 20" in FIG. 4.

The applicator body has an external surface of stainless steel between its proximal end 22 and its distal end. In particular, at least the external surface of body portion 20 is made of stainless steel; and, in the case of applicator 12, the body portion 20 is made entirely of stainless steel. It should be appreciated, however, that the body portion 20 does not have to be made of stainless steel in its entirety. For example, the wall forming body portion 20 can be composed of multiple layers including an outer or external layer of stainless steel and one or more inner or internal layers made of a material or materials other than stainless steel. Furthermore, the threaded proximal end of body portion 20 does not have to be made of stainless steel but, rather, can be made of a material or materials other than stainless steel, such as plastic, to facilitate manufacture. The tip 26 does not have to be made of stainless steel; and, accordingly, the tip 26 can be made of a material or materials other than stainless steel, such as plastic, to facilitate manufacture. Of course, at least the external surface of tip 26 can be made of stainless steel for optimum effectiveness, and the tip 26 can be made of stainless steel in its entirety.

The fluid supply tube 14 is preferably made of flexible, non-corrosive material, such as plastic, and has a length selected to facilitate use of the vaginal douche applicator 12 when the fluid supply tube 14 is used to connect the applicator 12 to a source of douching fluid (not shown). In accordance with the method of the present invention, the douching fluid is or includes water and, in particular, normal household water. Accordingly, a first end (not shown in FIG. 1) of fluid supply tube 14 is adapted to be connected to a source of water, such as a faucet tap, a shower tap or a household water supply line, for example. Of course, the first end of the fluid supply tube 14 can be provided with a suitable fitting to facilitate connection of the first end to the source. In addition, it should be appreciated that the first end of the fluid supply tube 14 or the fitting therefor can be designed or provided with structure for removable or permanent connection of the fluid supply tube 14 to the source. A second end of the fluid supply tube 14 terminates at a fitting 42. The fitting 42 has a longitudinal passage therethrough coupled with the lumen of tube 14. An open distal end 44 of fitting 42 is internally threaded for threaded connection to the coupling 18 as explained further below. As shown in FIG. 1, an external surface of the fitting 42 can be knurled or otherwise finished in order to facilitate grasping thereof.

The adapter 16 includes a cylindrical distal portion 46 and a cylindrical stem 48 extending proximally from the cylindrical distal portion 46. The stem 48 is longitudinally or axially aligned with the cylindrical distal portion 46, and a longitudinal passage 50 extends entirely through the adapter 16. The stem 48 has an external diameter smaller than an external diameter of cylindrical distal portion 46, and an external annular groove 52 is formed on the stem 48. The annular groove 52 extends continuously along an external circumference of stem 48 and is disposed distally of an open proximal end 54 of adapter 16. An open distal end 56 of adapter 16 is internally threaded and is designed for removable engagement with the external thread 30 of body portion 20. Accordingly, the longitudinal passage 50 of adapter 16 includes a distal passage section in cylindrical distal portion 46 having a diametric or cross-sectional size to receive the external diametric or cross-sectional size of the proximal end 22 of body portion 20 and includes a smaller diameter proximal passage section extending proximally from the distal passage section through the stem 48. A suitable washer or seal can be disposed in the distal passage section of passage 50 to prevent leakage of douching fluid when the adapter 16 is coupled to the applicator body and douching fluid is supplied through the passage 50 and the fluid passage 28 of the body portion 20.

Figure 5:
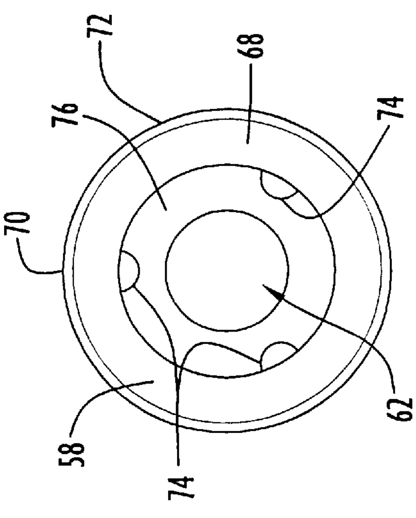
FIG. 5 is an end view of a coupling of the vaginal douche applicator assembly.

The coupling 18 is illustrated in FIGS. 1 and 5 and includes a cylindrical distal section 58 and a cylindrical proximal section 60 extending proximally from the cylindrical distal section 58 in longitudinal or axial alignment therewith. The cylindrical distal section 58 has an external diameter greater than an external diameter of the cylindrical proximal section 60, and a longitudinal passage 62 extends entirely through the coupling 18. The cylindrical proximal section 60, which terminates proximally at an open proximal end 66, has an external diametric or cross-sectional size to be received within the open distal end 44 of fitting 42 with an external thread 64 of cylindrical proximal section 60 in removable engagement with the internal thread of the fitting 42. The cylindrical distal section 58, which terminates distally at an open distal end 68, has a distal passage section of passage 62 therein. The distal passage section of passage 62 has a diametric or cross-sectional size for receiving the external diametric or cross-sectional size of stem 48 of adapter 16. The distal passage section of passage 62 communicates with a proximal passage section of passage 62 disposed in the cylindrical proximal section 60.

As shown in FIGS. 1 and 5, a collar or sleeve 70 is concentrically, slidably disposed over the cylindrical distal section 58. The collar 70 is biased by an internal spring of coupling 18 to be normally disposed in a longitudinally retracted position relative to cylindrical distal section 58. The longitudinally retracted position for collar 70 is illustrated in FIG. 1; and, in the longitudinally retracted position, a distal circumferential edge 72 of the collar 70 is aligned or substantially aligned with the open distal end 68. One or more holes or recesses are formed in an internal surface of cylindrical distal section 58, and a spherical ball 74 is disposed in each hole as shown in FIG. 4. Three holes are provided in cylindrical distal section 58 receiving three balls 74, respectively, the holes in cylindrical distal section 58 being provided at 120° spaced locations about a central longitudinal axis of coupling 18.

When the collar 70 is in the longitudinally retracted position, the balls 74 are biased in a radially inward direction to protrude into the distal passage section of passage 62 as shown in FIG. 5. However, when the collar 70 is manually moved distally relative to the cylindrical distal section 58 to a longitudinally extended position, the balls 74 are moved in a radially outward direction and are moved within or inside of the wall forming cylindrical distal section 58 so that the balls 74 no longer protrude into the distal passage section of passage 62. Movement of the collar 70 to the longitudinally extended position, wherein the distal edge 72 of the collar 70 is disposed distally beyond the open distal end 68, is accomplished manually via application of a manual force thereto; and, when the manual force is released, the collar 70 is automatically returned to the longitudinally retracted position due to the bias of the internal spring.

When the collar 70 is in the longitudinally retracted position, protrusion of balls 74 into the distal passage section of passage 62 prevents full insertion of stem 48 into the distal passage section of passage 62. However, when the collar 70 is moved distally while the stem 48 is moved proximally into the distal passage section of passage 62, the balls 74 are retracted into the wall of the cylindrical distal section 58. The stem 48 is then able to be fully inserted into the cylindrical distal section 58 such that the proximal end 54 of the stem 48 engages or abuts an internal annular end wall 76 within the coupling 18. When the proximal end 54 of stem 48 engages or abuts the end wall 76 of coupling 18, the groove 52 of stem 48 is in alignment with the balls 74. When the collar 70 is thereafter returned to the longitudinally retracted position, protrusion of the balls 74 into the distal passage section of passage 62 is now permitted since the groove 52 is aligned with the balls 74. Accordingly, the balls 74 enter the groove 52, and the adapter 16 is lockingly secured to the coupling 18. Since the balls 74 are biased into the groove 52, the adapter 16 cannot be moved longitudinally, distally or proximally, relative to the coupling 18, and the adapter 16 cannot be removed or separated from the coupling 18 until the collar 70 is moved from the longitudinally retracted position to the longitudinally extended position.

Preferably, the adapter 16, the coupling 18 and the fitting 42 are made of non-corrosive, strong materials such as stainless steel. Various types of conventional adapters and couplings can be used for the adapter 16 and the coupling 18, respectively. As an example, the adapter 16 and the coupling 18 can comprise the adapter and coupling of the Quick-Connect Set of Alsons Corporation of Hillsdale, Mich.

Prior to use, the vaginal douche applicator 12, the fluid supply tube 14, the adapter 16 and the coupling 18 are thoroughly washed or sterilized to ensure the cleanliness and sterility thereof. The applicator 12 is removably coupled with the adapter 16 via threaded engagement of external thread 30 of body portion 20 with the internal thread of adapter 16. The fluid supply tube 14 is removably coupled with the coupling 18 via threaded engagement of the external thread 64 of coupling 18 with the internal thread of fitting 42. The vaginal douche applicator 12 is removably coupled with the fluid supply tube 14 via engagement of stem 48 of adapter 16 by balls 74 of coupling 18 in response to manual movement of collar 70 to the longitudinally extended position as the stem 48 is moved proximally into the distal passage section of passage 62 as described above. Once the stem 48 is fully inserted in the distal passage section of passage 62, at which time the proximal end 54 of the stem 48 will be in abutment or engagement with the internal end wall 76 of coupling 18, the groove 52 will be in alignment with the balls 74. Upon release of collar 70 and automatic return of collar 70 to the longitudinally retracted position, the balls 74 will be moved inwardly into the groove 52, and the adapter 16 will be lockingly secured to the coupling 18. The first end of the fluid supply tube 14 is connected to a water source, such as a tap, nozzle, fluid supply line or other source for pressurized discharge of ordinary, unaltered household water, and the douche applicator assembly 10 is then ready to be utilized. Typically, the water source will have a valve or some other device for selectively turning the water source on and off, for selectively controlling the force or pressure of the discharged water and for selectively controlling the temperature of the discharged water. As a safety feature, a pressure regulator or reducer can be provided as part of the vaginal douche applicator assembly 10 to prevent douching fluid from being discharged therefrom with excessive pressure or force. As an example, the pressure reducer can be provided in or on the fluid supply tube and/or the fittings therefor.

Figure 6:
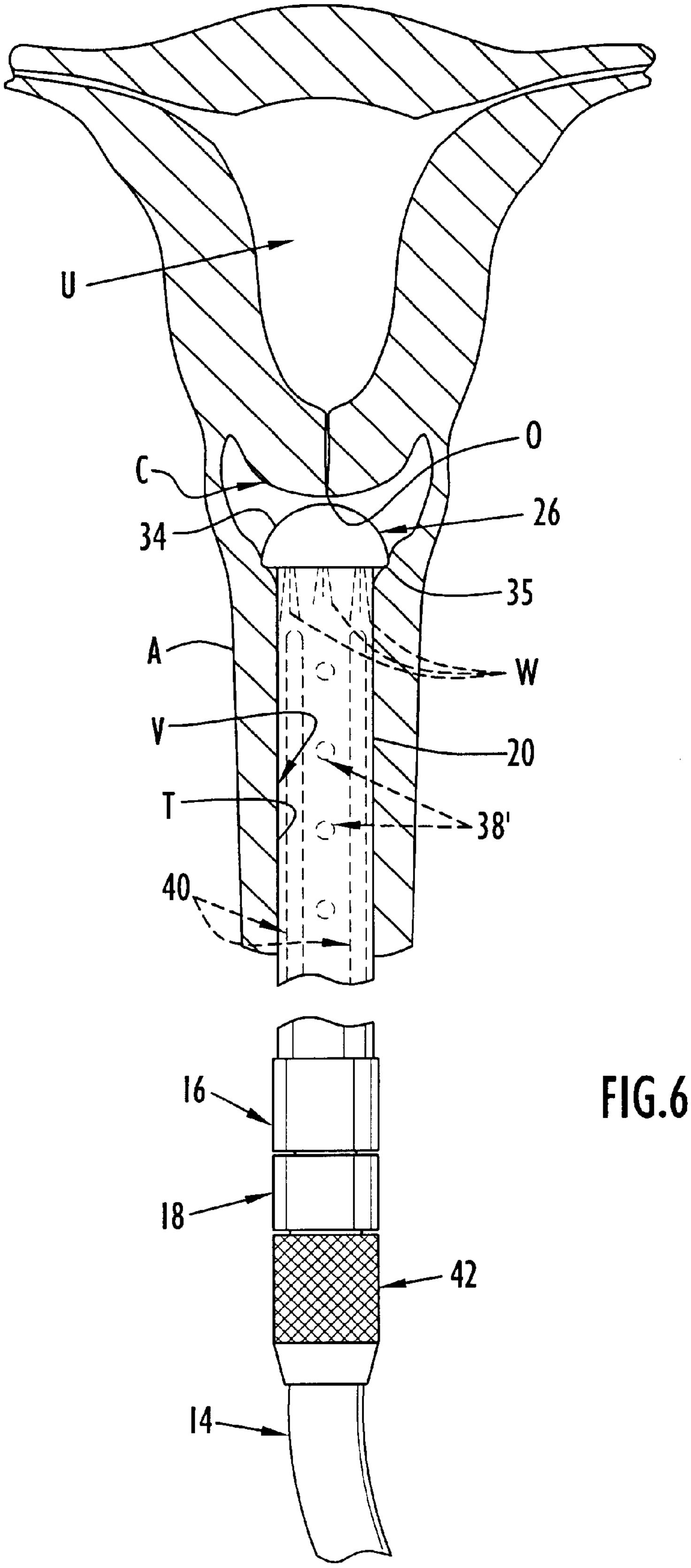
FIG. 6 is a broken view, partly in section, illustrating use of the vaginal douche applicator to neutralize vaginal odors.

In order to utilize the douche applicator assembly 10 for vaginal deodorization to neutralize or eliminate vaginal odors, the applicator 12 is manually inserted, tip first, by the user through the external vaginal opening and into the vaginal canal with the water source turned on or off. For some individuals, insertion may be more comfortable and may be executed more easily if the water source is on. As shown in FIG. 5, the vaginal douche applicator 12 is gently advanced distally or forwardly into the vaginal canal V as far as possible in accordance with the personal comfort of the user. The douche applicator 12 can be manually inserted, guided and positioned by the user grasping any or all of the fluid supply tube 14, the adapter 16, the coupling 18, the body portion 20 and/or the fitting 42. With the douche applicator 12 inserted in the vaginal canal V as far as desired by the user, the anatomical vaginal wall A forming the vaginal canal V will contract or compress around the applicator 12, due to the normal resiliency of the vaginal wall, such that the anatomical vaginal tissue T is in contact with the stainless steel external surface of the applicator 12. Accordingly, as shown in FIG. 6, the vaginal tissue T is in contact with the outer or external surface of body portion 20; and, where grooves 40 are provided, the tissue T is in contact with the convex body wall segments of body portion 20. The protuberant tip 26, being larger in diametric or circumferential size than the body portion 20, presents a protuberance, enlargement or obstruction located between the body portion 20 and the cervix C of the user. Preferably, the tip 26 is positioned adjacent the cervix and, depending on how far the applicator 12 is advanced into the vaginal canal V, the tip 26 may be disposed in abutment or contact with the cervix C. Since the tip 26 is diametrically or circumferentially larger than the body 20, the anatomical wall A will be contracted or compressed around the tip 26 more tightly or firmly than around the body 20 so that the tip 26 sealingly engages the wall A or is sealingly engaged by the wall A. In this manner, the tip 26 forms a seal in the vaginal canal V at the distal end of the applicator 12.

Once the applicator 12 is positioned as far as comfortable in the vaginal canal V, the water source is turned on. Cool water under pressure is transmitted through the fluid supply tube 14, the passage 62 of coupling 18, the passage 50 of adapter 16 and the lumen 28 of body 20 into the cavity 36 of tip 26. The water W is forcefully discharged from the applicator 12 into the vaginal canal through the holes 38 of tip 26 as shown in dotted lines in FIG. 6. The water W discharged from the holes 38 is directed toward the external vaginal opening and not toward the cervix C. In addition, the protuberant tip 26 forming a seal in the vaginal canal V prevents the water W from passing distally beyond tip 26 such that the water W cannot reach the cervix C. The seal formed by the protuberant tip 26 is disposed proximally of or at the same location or locations as the location for discharge of water W from the applicator 12 and therefore blocks passage of the water W to the external cervical os 0. In this manner, the water W, which constitutes the douching fluid, cannot enter the cervical canal and, therefore, also cannot enter the uterine cavity U of the user. It should be appreciated that, depending on how far the applicator 12 is advanced into the vaginal canal V, the tip 26 may actually be disposed in abutment with the cervix C to provide a direct physical barrier at the external cervical os 0. However, the protuberant tip 26 can be spaced proximally from the cervix C and still prevent water W from entering the external cervical os 0 due to the seal formed in vaginal canal V by the protuberant tip 26 engaging the vaginal wall A in sealing relation. The water W discharged from the applicator 12 flows proximally along the vaginal canal V in the direction of the external vaginal opening and exits or is discharged from the external vaginal opening. Discharge or exit of the water W from the vaginal canal V through the external vaginal opening is facilitated by the grooves 40 since the water W will flow within and along the grooves 40. Where additional holes 38' are provided in body portion 20, as shown in dotted lines in FIG. 6, the water W will also be discharged from the lumen 28 into the vaginal canal V through the holes 38'.

As the douching fluid, water W, is supplied under pressure through the applicator 12 for discharge into the vaginal canal V, the applicator 12 is manually manipulated by the user to insure contact of the vaginal tissue T with the stainless steel surface of the applicator 12. Typically, the applicator 12 will be turned or rotated about the longitudinal axis of body portion 20 to insure that the stainless steel surface contacts the entire or substantially the entire tissue T of the anatomical wall A, and the applicator 12 can also be moved longitudinally, distally and/or proximally, within the vaginal canal V in order to insure contact of the stainless steel surface with all or substantially all of the vaginal tissue. Where the applicator 12 is provided with grooves 40, rotation insures that all or substantially all of the tissue of wall A is contacted by the convex body wall segments. The roundness or curvature of forward wall 34 and the roundness or bluntness of the rim 35 and the lateral edges of grooves 40 prevent or avoid damage, trauma, irritation or other harm or injury to the tissue T as the applicator 12 is inserted in the vaginal canal V, as the applicator 12 is rotated and/or moved longitudinally within the vaginal canal V and as the applicator 12 is withdrawn from the vaginal canal V as explained further below.

Contact of the tissue T with the stainless steel surface of applicator 12 in the presence of water W discharged into the vaginal canal V from the applicator 12 results in neutralization or elimination of vaginal odors. The applicator 12 need only remain and be manipulated within the vaginal canal V for enough time to ensure that all or substantially all of the tissue T has been contacted by the stainless steel surface of the applicator in the presence of the water W. The applicator 12 can be manipulated within the vaginal canal V by the user grasping and moving any or all of the fluid supply tube 14, the adapter 16, the coupling 18, the body 20 and/or the fitting 42.

Upon completion of douching and deodorization of the vaginal canal in accordance with the present invention, the applicator 12 is removed or withdrawn from the vaginal canal V by the user grasping and gently pulling any or all of the fluid supply tube 14, the adapter 16, the coupling 18, the body portion 20 and/or the fitting 42. As the applicator 12 is withdrawn from the vaginal canal V, the protuberant tip 26 carries or directs water W present in the vaginal canal V toward the external vaginal opening for removal from the vaginal canal V as the tip 26 is withdrawn therefrom. Accordingly, the tip 26 performs a wiping or cleansing function on the vaginal tissue T as the applicator 12 is withdrawn from the vaginal canal V subsequent to douching. Upon withdrawal of the applicator 12 from the vaginal canal V, the applicator 12, the fluid supply tube 14, the adapter 16 and the coupling 18 are all preferably washed or sterilized, the douche applicator assembly 10 being designed for repeated use.

Figure 7:
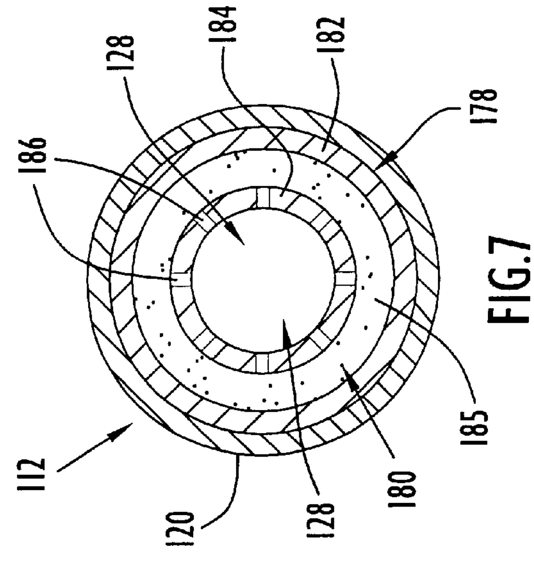
FIG. 7 is a cross-sectional view of the body portion of an alternative vaginal douche applicator according to the present invention.

The body portion 120 for an alternative douche applicator 112 according to the present invention is illustrated in FIG. 7. The alternative douche applicator 112 is the same as douche applicator 12 except that body portion 120 has a cartridge 178 disposed therein, the cartridge 178 containing a therapeutic substance 180 such as a medicament and/or a perfume. Cartridge 178 includes an outer annular wall 182 and an inner annular wall 184 concentrically disposed within outer annular wall 182. The outer annular wall 182 has an external diametric size the same as or substantially the same as the diametric size of passage 128 of body portion 120 such that the cartridge 178 is removably retained in the body portion 120 with a friction fit. The inner annular wall 184 has an external diametric size smaller than the internal diametric size of outer annular wall 182 such that there is a circumferential or annular gap or space 185 between the outer and inner annular walls. The therapeutic substance 180 is contained in the gap 185, and one or more holes or apertures 186 is/are formed in inner annular wall 184 establishing fluid communication between gap 185 and the fluid passage 128 of body portion 120.

The therapeutic substance 180 can initially be in various forms such as a soluble solid, gel, powder, granular or fluidic forms. Accordingly, when douching fluid is supplied to fluid passage 128 for douching as described above, the douching fluid will enter the gap 185 via holes 186 and will be combined with the therapeutic substance 180. Where the therapeutic substance 180 is in a solid or semi-solid form, the therapeutic substance 180 will be dissolved by the douching fluid and/or will be picked up and carried by the douching fluid. As the douching fluid is continuously supplied to fluid passage 128, douching fluid will also continuously flow into and out of the cartridge 178, i.e. gap 185, and the douching fluid discharged from the applicator 112 into the vaginal canal of the user will carry or contain the therapeutic substance 180. After use, the cartridge 178 can be removed, and a new cartridge can be installed in the applicator body prior to the next use. Alternatively, the cartridge 178 can be permanently installed in the applicator.

Figure 8:
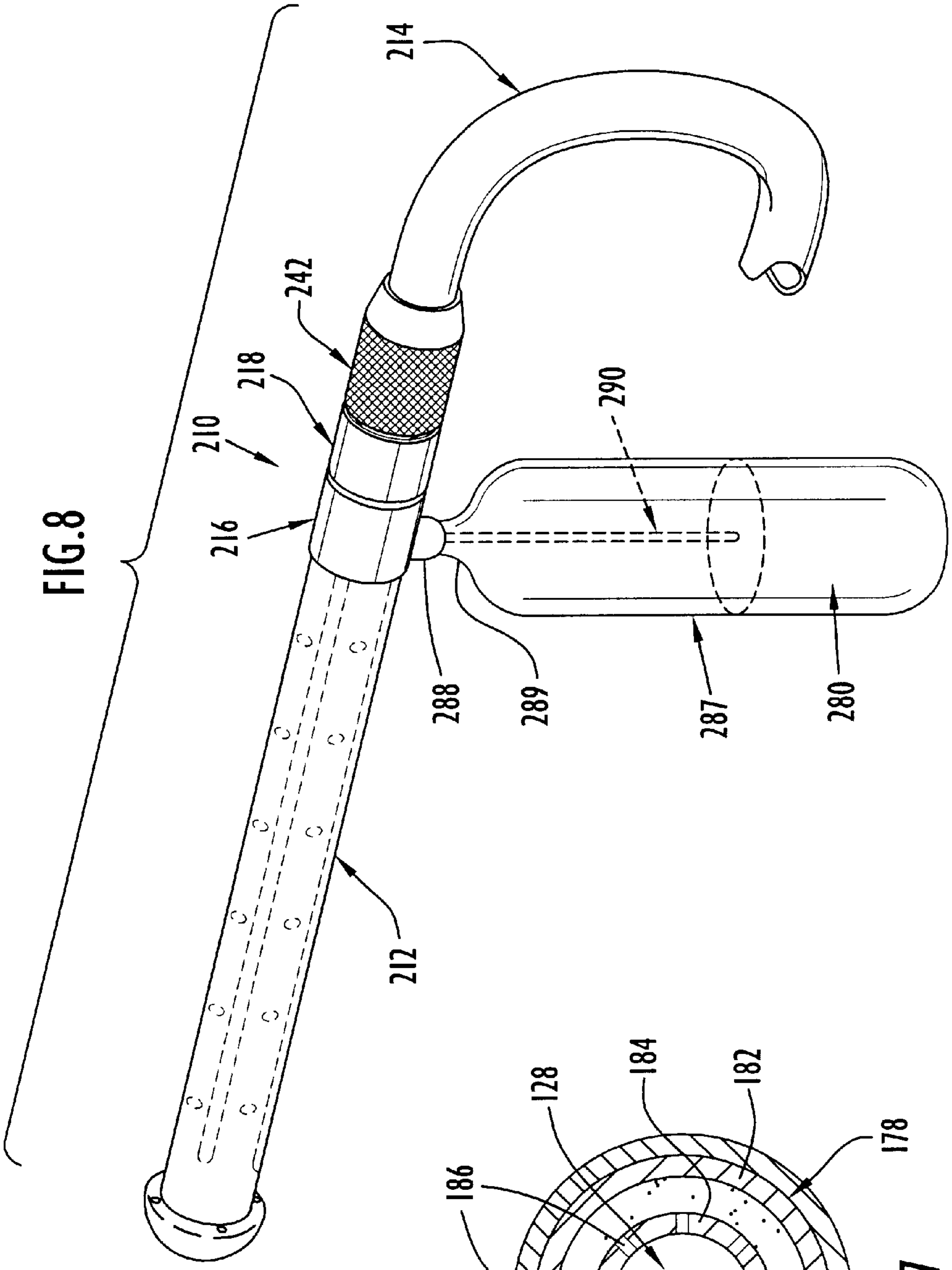
FIG. 8 is a broken perspective view of an alternative vaginal douche applicator assembly according to the present invention.

An alternative douche applicator assembly according to the present invention is illustrated at 210 in FIG. 8. The douche applicator assembly 210 is similar to douche applicator assembly 10 except that adapter 216 of douche applicator assembly 210 is attached to a bottle or container 287 coupled between douche applicator 212 and fluid supply tube 214. In particular, adapter 216 has a tubular or hollow stem 288 that is internally threaded for engagement with an external thread of neck 289 of bottle 287. Stem 288 is in communication with the passage through adapter 216 such that the interior of bottle 287 is in fluid communication with the fluid passage of applicator 212 when the adapter 216 is assembled to the applicator 212 as shown in FIG. 8. The interior of bottle 287 contains a therapeutic substance 280 in fluidic form, and a tube 290 extends from adapter 216 into the interior of bottle 287 and into the therapeutic substance 280.

The adapter 216 is assembled to the coupling 218 which, in turn, is assembled to the fitting 242 of fluid supply tube 214 as described above for vaginal douche applicator assembly 10. When douching fluid is supplied under pressure through fluid supply tube 214, a metered amount of therapeutic substance 280 is drawn through tube 290 and is combined with the douching fluid passing through adapter 216. Accordingly, the douching fluid is combined with the therapeutic substance prior to being supplied to the fluid passage of the applicator. The adapter 216 and/or the bottle 287 can be provided with a dial or other device for selectively controlling the amount of therapeutic substance 280 introduced into the douching fluid. Moreover, the adapter 216 and/or the bottle 287 can be provided with an appropriate valve and/or actuator for effecting introduction of therapeutic substance 280 into the douching fluid via tube 290. Of course, a pressure differential can be used to effect introduction of the therapeutic substance 280 into the douching fluid. The bottle 287 can be coupled between the applicator 212 and the fluid supply tube 214 in various ways using various different coupling mechanisms, fittings and/or adapters. It should be appreciated, therefore, that the douche applicator assembly 210 does not have to include the specific adapter 216, coupling 218 and/or fitting 242.

It should be apparent from the above that the douching fluid may consist entirely of water or may include water in combination with other substances, including fluidic substances combined with water as well as non-fluidic substances dissolved in or carried by water.

In accordance with the present invention, vaginal deodorization may be accomplished by douching with only normal household water being used as the douching fluid without any douching agents or substances being added thereto. However, the douching fluid can include water and other substances or fluids combined or mixed therewith and, in particular, therapeutic substances such as medicaments, perfumes and/or other desirable treating substances. Vaginal odors and the sources thereof are neutralized or eliminated due to contact of the stainless steel surface of the douche applicator with the vaginal tissue in the presence of water discharged into the vaginal canal by the applicator. The douche applicator according to the present invention presents or forms a seal in the vaginal canal obstructing the passage of douching fluid, discharged from the applicator, to the cervix. The protuberant tip of the applicator performs a wiping or cleansing function to the vaginal tissue as it is withdrawn from the vaginal canal, and may be positioned in the vaginal canal in a manner providing a physical barrier at the external cervical os.

Inasmuch as the present invention is subject to various modifications, additions or changes in detail, the preferred embodiments described herein should be considered illustrative only and should not be taken in a limiting sense since various modifications can be made thereto without departing from the scope of the invention as defined by the appended claims.

What is claimed is:

1. A method of vaginal deodorization comprising the steps of introducing a vaginal douche applicator in the vaginal canal;

supplying water to the vaginal canal through the applicator;

contacting the tissue of the vaginal wall with a stainless steel surface of the applicator as the water is supplied to the vaginal canal such that vaginal odors are neutralized due to contact of the tissue with the stainless steel in the presence of the water; and withdrawing the applicator from the vaginal canal.

2. A method of vaginal deodorization as recited in claim 1 wherein said step of introducing includes positioning a protuberant tip of the applicator adjacent the cervix.

3. A method of vaginal deodorization as recited in claim 2 wherein said step of positioning includes positioning the protuberant tip in contact with the cervix.

4. A method of vaginal deodorization as recited in claim 3 wherein said step of positioning includes positioning the protuberant tip over the external cervical os.

5. A method of vaginal deodorization as recited in claim 1 wherein said step of supplying includes supplying water under pressure to a fluid passage of the applicator and discharging the water from the fluid passage into the vaginal canal through a plurality of discharge holes formed in the applicator.

6. A method of vaginal deodorization as recited in claim 5 wherein said step of supplying includes supplying water in combination with another substance to the vaginal canal.

7. A method of vaginal deodorization as recited in claim 6 wherein said step of supplying includes combining the water with the another substance within the fluid passage of the applicator.

8. A method of vaginal deodorization as recited in claim 6 wherein said step of supplying includes combining the water with the another substance prior to supplying the water to the fluid passage.

9. A method of vaginal deodorization as recited in claim 5 and further including, prior to said step of introducing, coupling an open proximal end of the applicator with a source of water disposed externally of the vaginal canal.

10. A method of vaginal deodorization as recited in claim 9 wherein said step of coupling includes coupling the open proximal end to one end of a fluid supply tube and coupling another end of the fluid supply tube to the source of water.

11. A method of vaginal deodorization as recited in claim 2 wherein said step of supplying includes supplying water under pressure to an internal fluid passage of the applicator and discharging the waterfrom the fluid passage into the vaginal canal through a plurality of discharge holes formed in the protuberant tip in communication with the fluid passage.

12. A method of vaginal deodorization as recited in claim 11 wherein said step of positioning includes sealingly engaging the vaginal wall with the protuberant tip such that water discharged into the vaginal canal from the discharge holes is deterred from passing distally beyond the tip.

13. A method of vaginal deodorization as recited in claim 1 wherein said step of contacting includes rotating the applicator within the vaginal canal about a longitudinal axis of the applicator.

14. A method of vaginal deodorization as recited in claim 13 wherein said step of contacting further includes moving the applicator longitudinally within the vaginal canal.

15. A method of vaginal deodorization as recited in claim 1 and further including directing the water supplied to the vaginal canal to exit the vaginal canal through the external vaginal opening.

16. A method of vaginal deodorization as recited in claim 15 wherein said step of directing includes transporting the water, supplied to the vaginal canal, toward the external vaginal opening along external, longitudinally extending grooves of the applicator.

17. A method of vaginal deodorization as recited in claim 1 wherein said step of supplying includes supplying cool water to the vaginal canal.

* * * * *